US009020613B2

(12) United States Patent
Taylor et al.

(10) Patent No.: US 9,020,613 B2
(45) Date of Patent: Apr. 28, 2015

(54) METHOD AND APPARATUS FOR ROBOTICALLY ASSISTED COCHLEAR IMPLANT SURGERY

(71) Applicant: The Johns Hopkins University, Baltimore, MD (US)

(72) Inventors: Russell H. Taylor, Severna Park, MD (US); John Niparko, Glen Arm, MD (US); Iulian Ioan Iordachita, Towson, MD (US); Wade Wei-De Chien, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/874,555

(22) Filed: May 1, 2013

(65) Prior Publication Data

US 2013/0296884 A1   Nov. 7, 2013

Related U.S. Application Data

(60) Provisional application No. 61/640,950, filed on May 1, 2012.

(51) Int. Cl.
*A61N 1/00* (2006.01)
*A61B 19/00* (2006.01)

(52) U.S. Cl.
CPC ......... *A61B 19/2203* (2013.01); *A61B 19/5223* (2013.01); *A61B 2019/5234* (2013.01); *A61B 2019/505* (2013.01); *A61B 2019/508* (2013.01); *A61B 2019/5276* (2013.01)

(58) Field of Classification Search
USPC ....................................................... 607/137
See application file for complete search history.

(56) References Cited

U.S. PATENT DOCUMENTS

| 5,375,594 | A | 12/1994 | Cueva |
| 6,620,093 | B2 | 9/2003 | Waldmann et al. |
| 2010/0114288 | A1* | 5/2010 | Haller et al. ................. 607/137 |
| 2010/0255445 | A1 | 10/2010 | Gantes |
| 2011/0066160 | A1* | 3/2011 | Simaan et al. ............... 606/129 |
| 2011/0144749 | A1 | 6/2011 | Kim et al. |

FOREIGN PATENT DOCUMENTS

| WO | 2006118915 A2 | 11/2006 |
| WO | 2012040297 A2 | 3/2012 |
| WO | 2012040355 A2 | 3/2012 |

OTHER PUBLICATIONS

Of "A Steady-Hand Robotic System for Microsurgical Augmentation" Taylor et al., International Journal of Robotics Research, 18(12):1201-1210 Dec. 1999, (Author is one of present Inventors).*

(Continued)

*Primary Examiner* — Robert N Wieland
(74) *Attorney, Agent, or Firm* — Johns Hopkins Technology Transfer

(57) ABSTRACT

A novel sensing system and methods for preventing damage to the cochlea during cochlear implant surgery are disclosed, using optical sensing to determine the distance of a stylet or the end of the implant itself from the interior wall of the scalar tympani. A variety of feedback methods are proposed to enable the surgeon to perform the procedure safely without damage to the basilar membrane or other delicate anatomic structures. Although a number of embodiments are disclosed, one preferred embodiment comprises a robotically manipulated end-effector.

52 Claims, 8 Drawing Sheets

(56) References Cited

OTHER PUBLICATIONS

Schurzig, D., et al., "A force sensing automated insertion tool for cochlear electrode implantation", IEEE International Conference on Robotics and Automation, (2010) pp. 3674-3679.

Zhang, J., et al., "A pilot study of robot-assisted cochlear implant surgery using steerable electrode arrays", Med Image Comput Comput Assist Interv (2006) vol. 9, Pt. 1, pp. 33-40.

Zhang, J., et al., "Inroads toward robot-assisted cochlear implant surgery using steerable electrode arrays", Otology and Neurotology (2010) vol. 31, pp. 1199-1206.

Zhang, J., et al., "Path planning and workspace determination for robot-assisted insertion of steerable electrode arrays for cochlear implant surgery", Med Image Comput Comput Assist Interv (2008) vol. 11, Pt. 2, pp. 692-700.

Vlastarakos, P., et al., "Cochlear implantation update: contemporary preoperative imaging and future prospects—the dual modality approach as a standard of care" Expert Rev Med Devices (2010) vol. 7, Iss. 4, pp. 555-567.

Stelter, K., et al., "Image guided navigation by intraoperative ct scan for cochlear implantation", Computer Aided Surgery, May 2012, vol. 17, Iss. 3, pp. 153-160.

Radeloff, A., et al., "Intraoperative monitoring using cochlear microphonics in cochlear implant patients with residual hearing", Otology & Neurotology (2012) vol. 33, pp. 348-354.

Reda, F., et al., "Automatic pre- to intra-operative ct registration for image-guided cochlear implant surgery" IEEE Transactions on Biomedical Engineering (2012) vol. 59, No. 11, pp. 3070-3077.

Kahrs, L., et al., "Measurement of distances between anatomical structures using a translating stage with mounted endoscope", Image-guided Procedures, Robotic Interventions, and Modeling (2012) vol. 8316, 7 pages.

Mangos, B., et al., "Surgical techniques in cochlear implants", Otolaryngol Clin N Am (2012) vol. 45, pp. 69-80.

International Search Report and Written Opinion, mailed Sep. 25, 2013; PCT/US2013/038989, filed May 1, 2013.

Rau, T., et al., "Accuracy of computer-aided geometric 3D reconstruction based on histological serial microgrinding preparation", Computer Methods in Biomechanics and Biomedical Engineering, (2001) 14:7, 581-594.

\* cited by examiner

METHOD AND APPARATUS FOR ROBOTICALLY ASSISTED COCHLEAR IMPLANT SURGERY

CROSS REFERENCE TO RELATED APPLICATIONS

This application claims the benefit of U.S. Provisional Patent Application No. 61/640,950 filed on May 1, 2012, which is incorporated by reference, herein, in its entirety.

FIELD OF THE INVENTION

The present invention relates generally to surgery. More particularly, the present invention relates to a method and device for improved robotically assisted cochlear implant surgery.

BACKGROUND OF THE INVENTION

Cochlear implant surgery can be an immense auditory, linguistic and developmental benefit to patients with severe hearing deficiencies caused by the loss of hair cell transduction within the cochlea. The surgical procedure is potentially complicated by difficulties with implanting electrode array insertion and serious complications may occur.

One particularly challenging step is the actual insertion of the implant into the cochlea. After accessing the scala tympani (via direct round window insertion, or drilling open a cochleostomy to gain access to the cochlea), an electrode array is inserted into the scala tympani of the cochlea. Several designs of cochlear implant arrays have relied on stylet-based insertion techniques.

Over the past 6 years, the Cochlear Corporation Freedom and C512 arrays have used a stylet-based strategy. In particular, a stylet is used to hold the implant straight while it is inserted to a desired depth into the cochlea. The array is advanced over the stylet, which is held in a fixed position. The implant naturally curves to follow the cochlea. The stylet is then withdrawn. If the stylet and implant are advanced too far into the cochlea, the resulting contact forces can damage the cochlea. There is also research to replace the stylet with a sheath around the electrode array to hold it straight while the implant is inserted down the scala tympani of the cochlea. One example of such a sheath is the Modiolar Research Array (R. Briggs et al., "Development and evaluation of the modular research array—multi-centre collaborative study in human temporal bones", Cochlear Implants Int. 2011 Aug. 12 (3) pp. 129-139, PMCID: PMC3159433).

Several approaches to providing guidance or assistance in avoiding damage to the cochlea during implant insertion have been reported recently. In particular, Schurzig, Labadie, and Webster report a system that combines an "active cannula" robot with delicate force sensing capabilities to sense contact between the implant and the cochlea, using a force sensor incorporated into the robotic mechanism that advances the implant into the cochlea. D. Schurzig, R. F. Labadie, and R. J. Webster, "A force sensing robot for cochlear electrode implantation", in IEEE International Conference on Robotics and Automation, 2010, pp. 3674-3679. Rau et al. have also proposed a robotic cochlear insertion device and have reported phantom studies of insertion forces using a load cell attached to the insertion mechanism.

Zhang, Simaan, et al. have developed an actively deforming, steerable, cochlear implant that curves to follow the cochlea during insertion. See e.g., J. Zhang, W. Wei, S. Manolidis, J. T. Roland, Jr., and N. Simaan, "Path planning and workspace determination for robot-assisted insertion of steerable electrode arrays for cochlear implant surgery", Med Image Comput Comput Assist Interv, vol. 11—Pt 2, pp. 692-700, 2008; J. Zhang, K. Xu, N. Simaan, and S. Manolidis, "A pilot study of robot-assisted cochlear implant surgery using steerable electrode arrays", Med Image Comput Comput Assist Interv, vol. 9—Pt 1, pp. 33-40, 2006; J. Zhang, W. Wei, J. Ding, J. T. Roland, S. Manolidis, and N. Simaan, "Inroads Toward Robot-Assisted Cochlear Implant Surgery Using Steerable Electrode Arrays", Otology and Neurotology, p. in Press; Published ahead of print, 2010 10.1097/MAO.Ob013e3181e7117e. They report experiments using a load cell mounted on their robotic manipulation device. Some limitations of these systems include reliance on a fairly large and cumbersome robotic insertion tool and the necessity to implement an extremely delicate force sensing mechanism. In the case of the reported systems, the difficulty is exacerbated by the moving mass of the mechanism distal to the force sensor and possible friction forces.

Other authors have proposed robotic devices to assist in drilling the skull to gain access to the cochlea for implant insertion. These systems do not address the problem of inserting an implant without damage to the cochlea. See, e.g., C. J. Coulson, R. P. Taylor, A. P. Reid, M. V. Griffiths, D. W. Proops, and P. N. Brett, "An autonomous surgical robot for drilling a cochleostomy: preliminary porcine trial", Clin Otolaryngol, vol. 33-4, pp. 343-7, August 2008; and O. Majdani, D. Schurzig, A. Hussong, T. Rau, J. Wittkopf, T. Lenarz, and R. F. Labadie, "Force measurement of insertion of cochlear implant electrode arrays in vitro: comparison of surgeon to automated insertion tool", Acta Oto-Laryngologica, vol. 130-1, pp. 31-36, January 2010.

Skilled otologic surgeons have the manual dexterity and steadiness to insert implants without damage to the cochlea. What they lack is feedback to know when the implant or stylet has been introduced too far into the cochlea. See, e.g., C. J. Coulson, A. P. Reid, D. W. Proops, and P. N. Brett, "ENT challenges at the small scale", Int J Med Robot, vol. 3-2, pp. 91-6, June 2007.

Accordingly, there is a need in the art for a system that allows a surgeon information regarding the location of the implant with respect to the cochlea walls.

SUMMARY OF THE INVENTION

The foregoing needs are met, to a great extent, by a method for robotically assisted implant surgery for cooperatively controlled robots. The method includes scanning a narrow cavity in a patient's body with an imaging device and forming a model of the cavity. A cooperatively controlled robot is used to manipulate an implant and an implant delivery device into the cavity, using models of the cavity to implement virtual fixtures.

In accordance with an aspect of the present invention, a system for robotically assisted implant surgery for a cooperatively controlled robot, includes a tool holder for receiving a surgical tool, imaging device, or implant adapted to be held by the cooperatively controlled robot and a surgeon. An imaging device is included for scanning a narrow cavity in a patient's body, and a processor is included for forming a model of the cavity based upon images from the imaging device.

In accordance with another aspect of the present invention, a tooling device for cooperatively controlled robots, includes a tool holder a surgical tool, imaging device, or implant adapted to be held by a robot and a surgeon. The tooling device also includes a first grasper for holding an implant delivery device. A second grasper is included for holding an electrode array of an implant. The second grasper also includes means for allowing engagement and disengagement of the electrode array. Additionally, the first and second graspers are mounted on a rotational stage. The rotational stage includes an aperture along an axis of a microscope to be viewed by the surgeon.

BRIEF DESCRIPTION OF THE DRAWING

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a method and device for improved robotically assisted cochlear implant surgery. More particularly, the present invention pertains to using a scanning OCT probe held by a cooperatively controlled steady-hand robot to image and model the scala of the cochlea. The probe is then removed and the robot will be used to position the implant into the scala of the cochlea and hold it in place, while it is deployed off the robot. This concept is relatively straightforward to implement, does not require any modification of the traditional electrode array, maximizes synergy with the initial OCT scanning study, and will promote development and integration of hardware, software, and user interfaces that can be adapted to other approaches in future work, based on the experience gained.

Figure 1A:
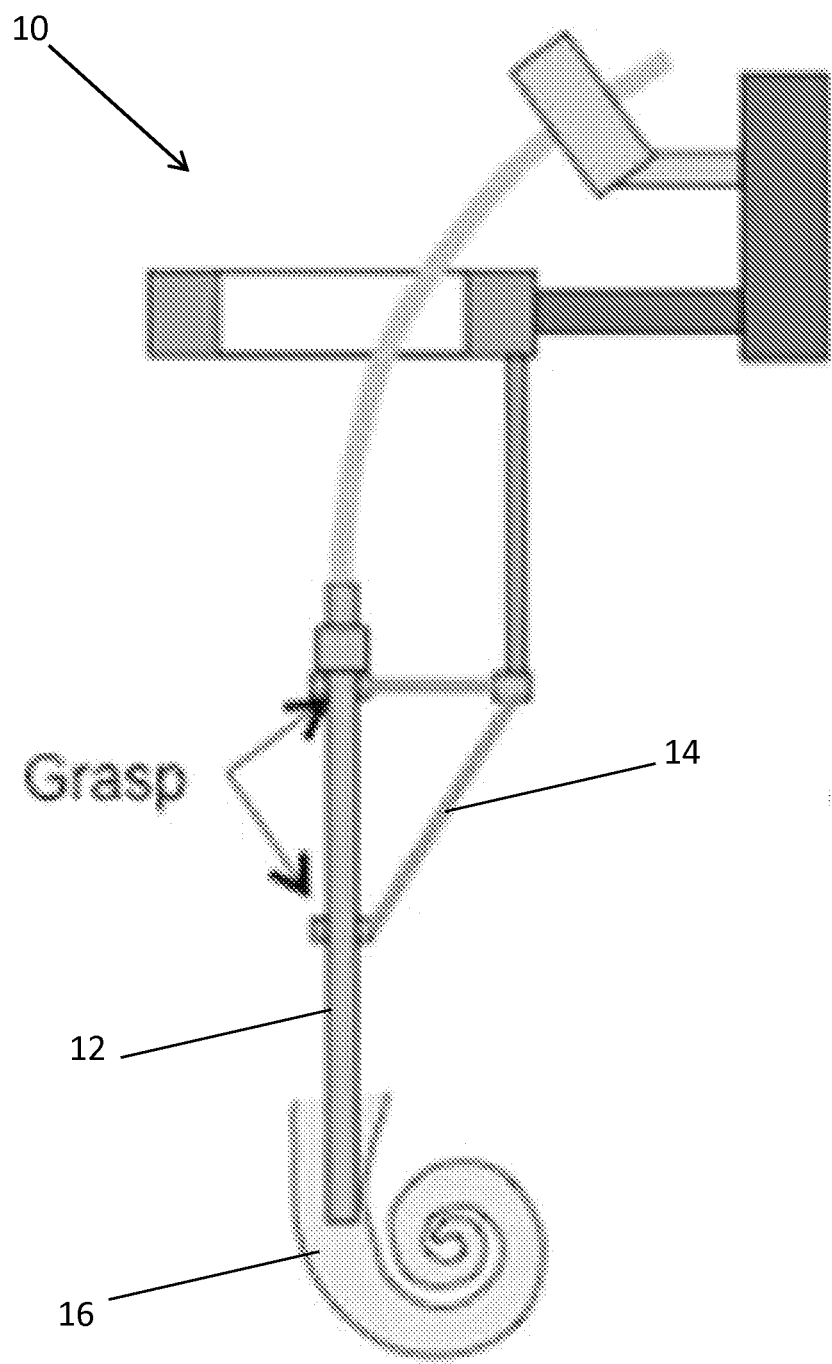
FIGS. 1A-1D illustrate schematic diagrams of a tooling concept and procedure workflow for robotically assisted cochlear implant surgery according to the features of the present invention.
Figure 1B:
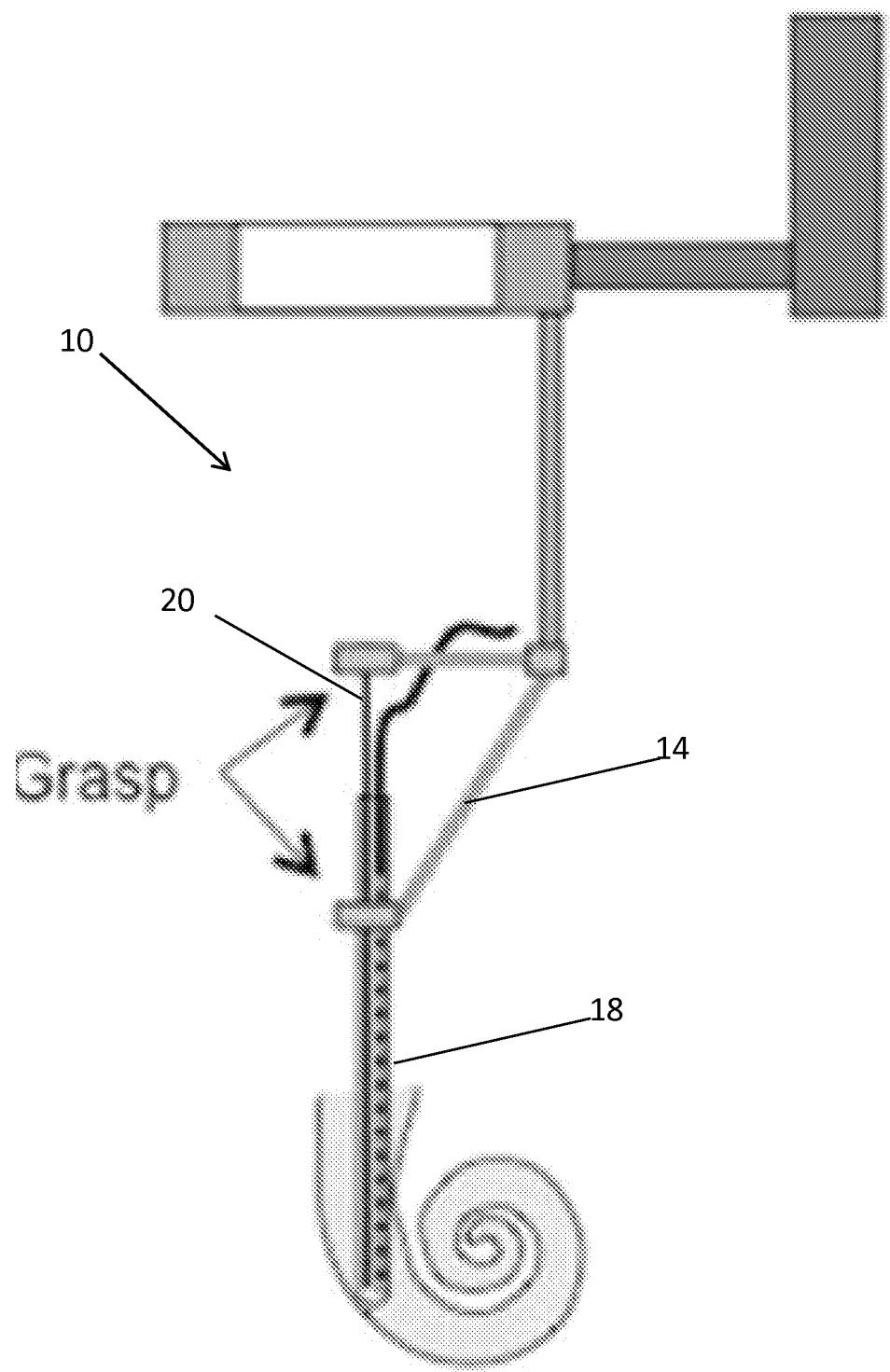
Figure 1C:
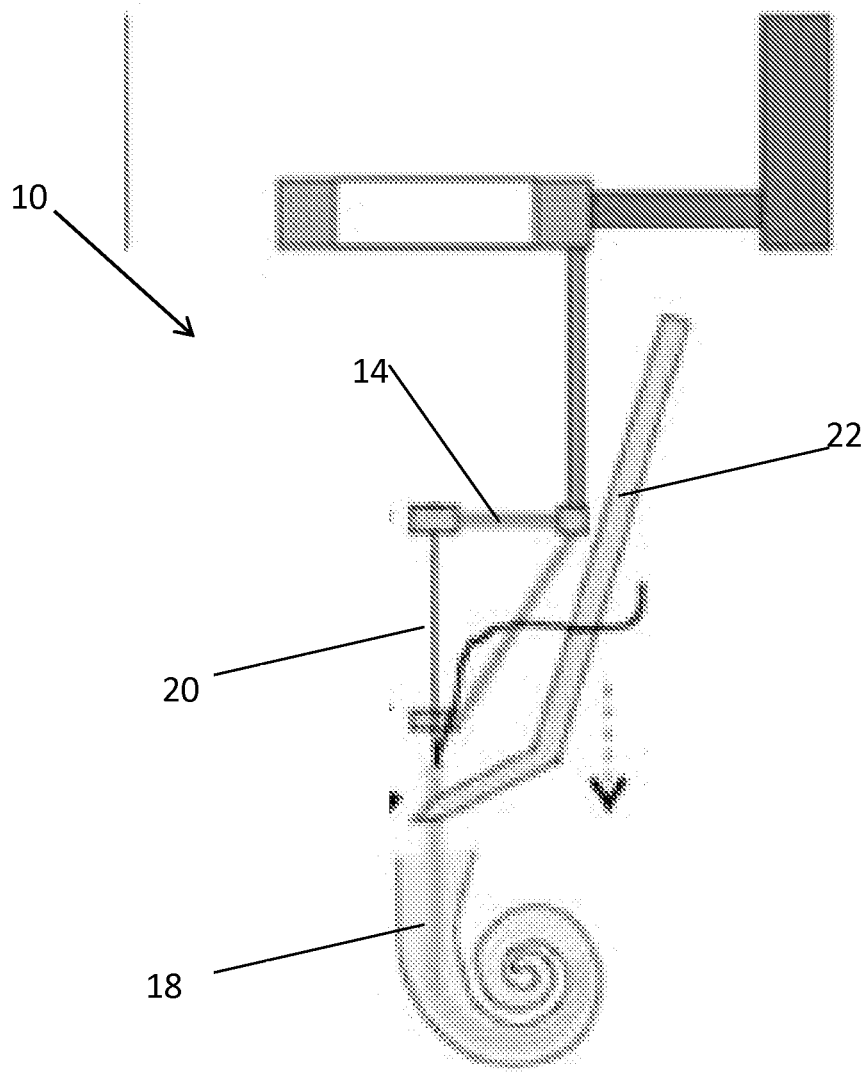
Figure 1D:
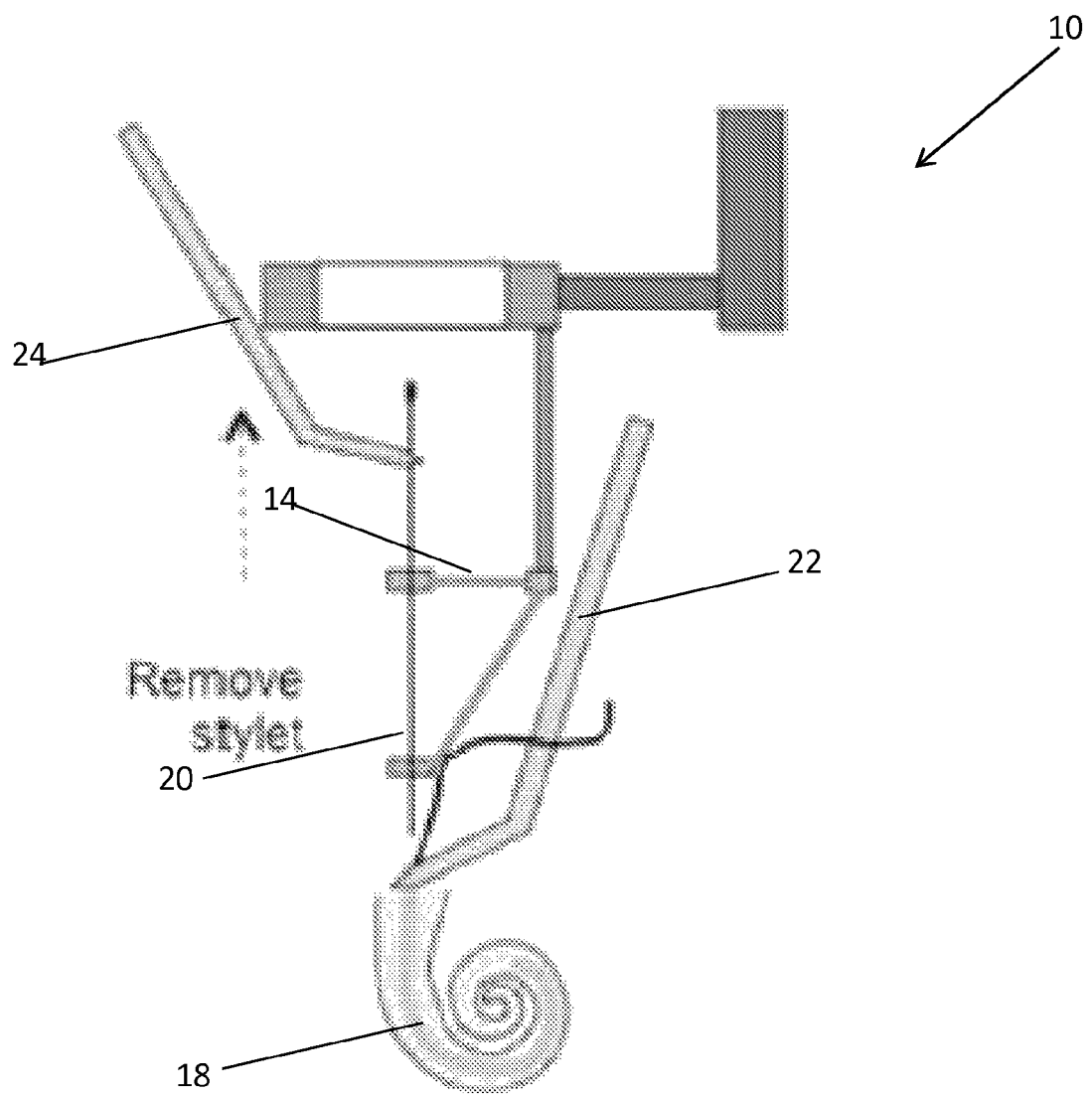

FIGS. 1A-1D illustrate schematic diagrams of steps of a procedure for robotically assisted cochlear implant surgery. More particularly, FIG. 1A illustrates a schematic diagram of a scan of a scala of the cochlea with a robot end-of-arm tooling holding an imaging probe. A model of the scala of cochlea is created in robotic coordinates to illustrate the axis of the scala, angle of the scala, depth to turn for the scala, and other relevant features known to or conceivable by one of skill in the art. FIG. 1B illustrates a schematic diagram of the robot end-of-arm tooling to be used with a robot to manipulate a cochlear implant and an implant delivery device, such as an implantation stylet, sheath, other similar structure, or device for delivering an implant known to or conceivable by one of skill in the art. As illustrated in FIG. 1B, and by way of example, the implant delivery device takes the form of a stylet. The model of the scala created and described with respect to FIG. 1A is used to implement virtual fixtures to assist in insertion and to enforce depth to turn. Although not illustrated, the manipulation of the cochlear implant and implant delivery device into the scala can also be displayed to the physician and surgical team. FIG. 1C illustrates a schematic diagram of a release of the cochlear implant. The robot end-of-arm tooling continues to hold the stylet, and a hand tool can then be used to deploy the implant off of the stylet. Alternately, the robot end-of-arm tooling can be used to deploy the implant off of the stylet in a stripping motion, while continuing to hold the stylet. FIG. 1D illustrates a schematic diagram of the release of the stylet. A second hand tool can be used to remove the stylet. However, the robot can also be programmed to remove the stylet via the robot end-of-arm tooling.

Further with respect to FIG. 1A, the robot end-of-arm-tooling device 10 includes a scanning probe 12 is placed in the tool holder 14 in a known position. Using "steady hand" guiding, the surgeon guides the probe into the one of the cochlear scalae 16 while observing the probe under the surgical microscope. As the probe is slowly inserted into the scala, the system will build up a 3D OCT model of the canal. Any other known modeling modality known to or conceivable by one of skill in the art could also be used. For example, the robot may hold an OCT scanning device that can image the scala without the requirement that a probe actually be inserted into the scala. Alternatively, an OCT scanning device may operate through a surgical microscope and image both the scala and fiducial geometry held in a known position and orientation relative to robot coordinates. Similarly, an ultrasound imaging device may be used.

The robot probe holder will be calibrated so that the position of the resulting scans and model are known relative to robot coordinates. As the model is built up, it may be displayed to the surgeon on a video monitor, who can use this information to help guide the probe into the canal and also to know when to stop inserting. It is also possible that the computer uses this information to provide auditory cues and/or "virtual fixtures" to assist in maintaining the probe alignment as the probe is inserted into the scala. Scanning and insertion will stop when the model of the scala is complete down to the first turn. The probe will then be withdrawn from the scala and removed from the probe holder.

With respect to FIG. 1B, an electrode array 18 of the surgical implant will then be grasped by the tool holder 14 for the device 10. In the present invention, discussed more below, the robot tooling will grasp the stylet 20 and a second point on the electrode array 18 in order to provide firm control of the implant and its direction. The surgeon will guide the electrode array 18 into the scala using "steady hand" guiding with the robot with direct visual guidance through the surgical microscope. A variety of information supports will be available to the surgeon to assist in positioning the electrode array so that the array is properly positioned and oriented to begin deployment off the stylet 20. These may include a combination of computer graphical displays based on the 3D cochlear scalae model/image produced by the probe, as described with respect to FIG. 1A, auditory cues based on the relative position of the implant to the desired trajectory, and haptic "virtual fixtures" to assist in maintaining the correct alignment and in preventing the implant from being advanced too far.

Virtual fixtures are well known in the robotic art. Treatments may be found in: 1) J. Funda, R. Taylor, B. Eldridge, S. Gomory, and K. Gruben, "Constrained Cartesian motion control for teleoperated surgical robots", *IEEE Transactions on Robotics and Automation*, vol. 12-3, pp. 453-466, 1996; 2) M. Li, M. Ishii, and R. H. Taylor, "Spatial Motion Constraints in Medical Robot Using Virtual Fixtures Generated by Anatomy", *IEEE Transactions on Robotics,* vol. 23-1, pp. 4-19, 2007 3) A. Kapoor, *Motion Constrained Control of Robots for Dexterous Surgical Tasks*, Ph.D. thesis in Computer Science, Johns Hopkins University, Baltimore, 2007. However, there are also numerous other treatments providing a variety of approaches to implementation of virtual fixtures. Any suitable implementation may be used.

Alternately, the tooling and software infrastructure is designed to support the use of a "sensing stylet" or "sensing electrode array" as the implant delivery device. An OCT fiber can also be used as the implant delivery device.

FIG. 1C illustrates a schematic diagram of the robot tooling of the device 10 that will release the implant electrode array 18, while continuing to hold the stylet 20 firmly in the deployment position. The surgeon will use a conventional hand tool 22 to deploy the electrode array 18 from the stylet 20 while the robot maintains the position of the stylet 20. This approach helps to facilitate a key requirement to maintain the proper position of the stylet 20 during deployment. This approach will also establish the infrastructure and a starting point for alternative refinements, if they should be necessary.

Alternately, with respect to FIG. 1C, it is possible to modify the hardware to permit deployment of the implant using the portion of the tooling that grasps the electrode array by placing this component on a sliding member, which may be manually or robotically actuated. Also, it is possible to incorporate force feedback into the system as a further aid to atraumatic deployment. The most straightforward way to do this would be to replace the conventional hand tool with force sensing forceps that reporting the sensed forces to the surgeon with auditory or visual feedback. Force sensors can also be incorporated into robot tooling used to deploy the array off the stylet.

FIG. 1D illustrates a schematic diagram showing the device 10 after the electrode array 18 is deployed. Further, after the electrode array 18 is deployed, the stylet 20 will be removed. This may be accomplished either by ungrasping it from the tooling and removing it with a hand tool 24 in the conventional manner while holding the array 18 in place or by using the robot.

Figure 2:
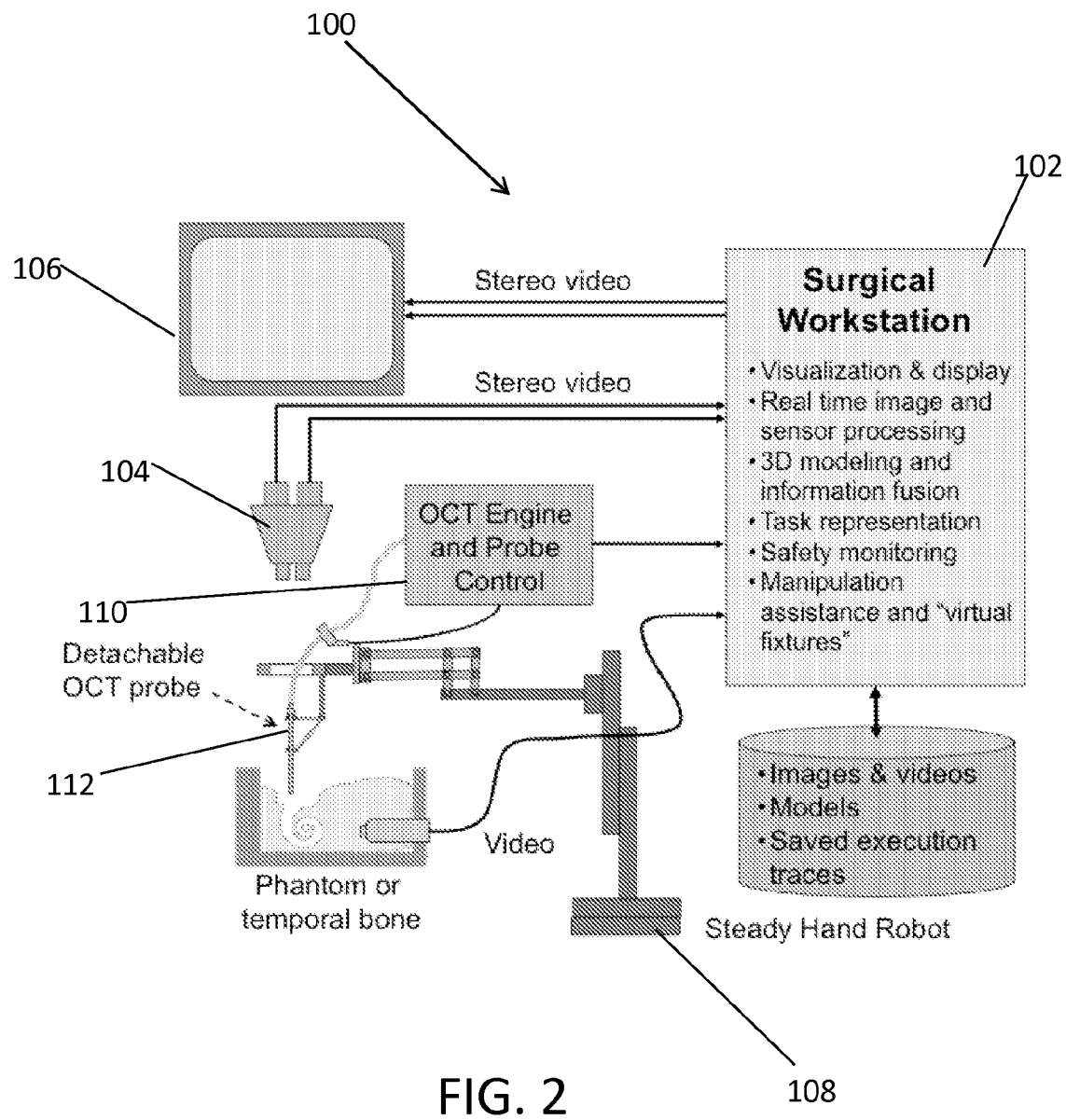
FIG. 2 illustrates a schematic diagram of a system for robotically assisted cochlear implant surgery according to features of the present invention.

FIG. 2 illustrates a schematic diagram of an overview of an exemplary embodiment of the system of the present invention. The system 100 includes a surgical workstation 102 that is in wireless, networked, or directly wired communication with a surgical microscope 104, a display 106, and a steady-hand robot 108. Each of the surgical microscope 104, display 106, and steady-hand robot 108 is in communication with the workstation 102, but can also be configured to be in communication with each other using networking, wiring, and microprocessors known to or conceivable by one of skill in the art. The surgical microscope 104 can take the form of a stereo-video surgical microscope, or any other suitable surgical microscope known to or conceivable by one of skill in the art. The system 100 can also include an OCT system 110 including a detachable OCT probe 112 for images, video, and modeling of the surgical field.

More particularly, with respect to the system 100 illustrated in FIG. 2, the heart of the system is the surgical workstation computer 102. The surgical workstation computer can include an extended version of a CISST/SAW software environment ("Surgical Assistant Workstation (SAW) software", Johns Hopkins University, Open source software for medical robotics research, www.cisst.org/saw). While the CISST/SAW software environment is given as an example, any software environment suitable for the implementation of the cochlear implant surgery known to or conceivable by one of skill in the art could also be used. The exemplary CISST/SAW system supports functions such as video acquisition from the surgical microscope 104 and other sources, video image processing, stereo and monoscopic video display with graphic overlays, capture of sensor and image data from OCT and other devices, control of robots and other devices, higher-level functions such as virtual fixtures & auditory cues, and the ability to generate a time-stamped, synchronized log of all information and activity during the surgery.

Also illustrated in FIG. 2, the stereo video surgical microscope 104 is equipped with stereo video capture and display capabilities on display 106. The surgeon has the option of viewing the surgical field through the microscope optics or through the display 106. The display 106 can be configured in any number of ways known to or conceivable by one of skill in the art. The display can also be configured to wirelessly receive any information to be displayed, such that it can be placed in or repositioned to any necessary position in the surgical theater. The system 100 illustrated in FIG. 2 also includes a cooperatively controlled steady-hand robot 108 for assisting with the cochlear implant surgery. Here, "cooperative control" refers to the ability of the surgeon to provide interactive input to the system to affect the motion of the robot's end effector during task execution. In cooperative control, both computer controlling the robot's actuators and the surgeon can directly influence the motion. Some motions may be entirely directed by the surgeon through teleoperation or "steady hand" control (discussed below) and others may be influenced by "virtual fixtures" or otherwise partially specified by the robot control computer. The balance between the surgeon's input and the computer may vary from motion to motion.

In cooperative steady-hand robot control, both the robot and surgeon hold tooling attached to the robot's end effector. A force sensor detects forces exerted by the surgeon and the robot moves to comply. However, this compliant behavior may be modified by "virtual fixtures", which are well known in the robotic art, based on sensor values or task geometry. Alternative means of robot control, such as conventional teleoperation, may also be used, and the robot behavior can be modified by means of virtual fixtures to help the surgeon achieve the desired task.

Further with respect to FIG. 2, the system architecture supports a variety of OCT systems 110, known to or conceivable by one of skill in the art. The robot 108 and overall system 100 also can be used to support the acquisition of 3D OCT volumes, images and videos, models, and saved execution traces. A variety of force sensing instruments known to or conceivable by one of skill in the art can also be used in conjunction with the system illustrated in FIG. 2. More particularly, one of these force sensing tools (e.g., a force-sensing forceps tool) can be used to monitor forces during deployment of the electrode array off the stylet. In cases where the system 100 is used for surgical practice or system testing, both an artificial phantom equipped with a video camera and fixed human temporal bones can also be used to support the video and modeling aspects of the present invention. The video will be captured by the workstation and synchronized with other acquired data for offline analysis.

Figure 3:
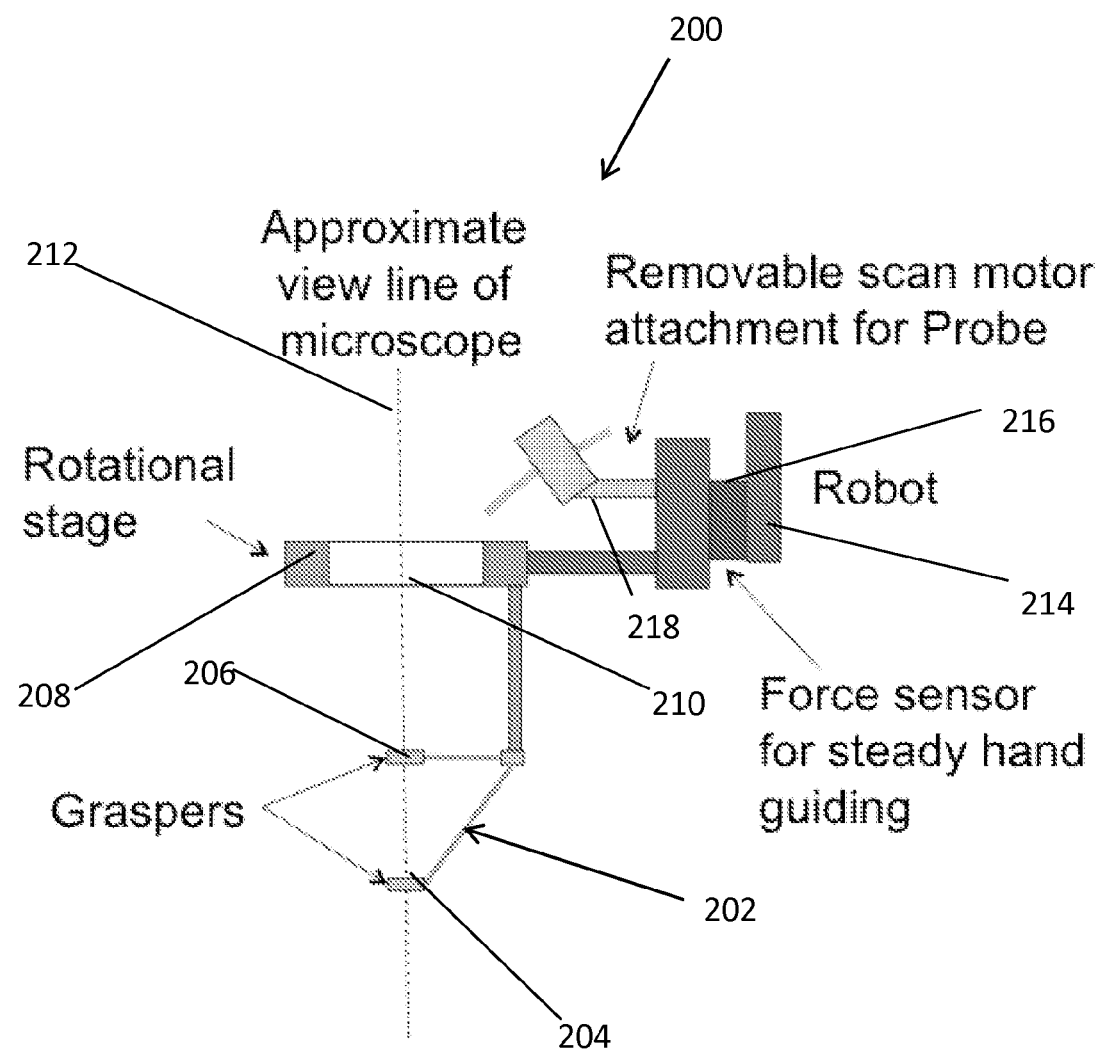
FIG. 3 illustrates an end of arm tooling device to be used in connection with the system and apparatus of the present invention.

FIG. 3 illustrates a schematic diagram of a customized robotic arm tool for use with the system and method of the present invention. The system 200 includes the customized robotic arm tool ("tool") 202. The tool 202 includes a distal grasper 204 and a proximal grasper 206. The tool 202 is, therefore, capable of grasping both the implant delivery device, shown here as a stylet and the proximal portion of the electrode array (not pictured). At least the distal grasper 204 (the one that holds the electrode array) is configured to be able to engage and disengage. The distal and proximal graspers 204, 206 are mounted on a rotational stage 208 with a large hole 210 to allow observation along the electrode array axis 212 from the microscope (not pictured). The rotational stage 208 can be manually actuated and may be used to orient the electrode array about the insertion axis 212 so that the array is properly aligned relative to the turn of the scala. Alternately, the rotational stage 208 can include robotic control 214, as well.

Although it is not illustrated in FIG. 3, the tool 202 also can have a handle for the surgeon to grasp to facilitate manipulation. A force sensor 216 can also be included with the robotic control 214 for steady-hand guiding of the tool 202. In addition, there is an attachment point 218 for the OCT probe scan motor (not pictured). The probe itself is constructed such that the tool 202 can grasp it in a very repeatable manner, and the probe includes a flexible shaft to minimize interference with the view through the microscope. Known OCT probes can be used in conjunction with the present invention. However, it is also possible that an OCT probe conceivable by one of skill in the art and optimized for the present invention could also be used.

Although the workflow described above describes the use of a scanning probe for imaging the scala, other means may be substituted for this purpose. These include an imaging bundle probe held by the robot, an ultrasound probe held by the robot, x-ray, cone beam CT (CBCT) or conventional CT images registered to the robot and patient, or any imaging modality providing 3D images of the scala registered to the robot and patient. Also, it will be readily apparent that the tooling described may be combined with the sensing stylet or any of the robotic embodiments disclosed in "Optical Sensing System for Cochlear Implant Surgery," U.S. patent application Ser. No. 13/238,538; and "Method and Apparatus for Cochlear Implant Surgery", U.S. patent application Ser. No. 13/239,803, both disclosures of which are incorporated by reference herein.

Figure 4:
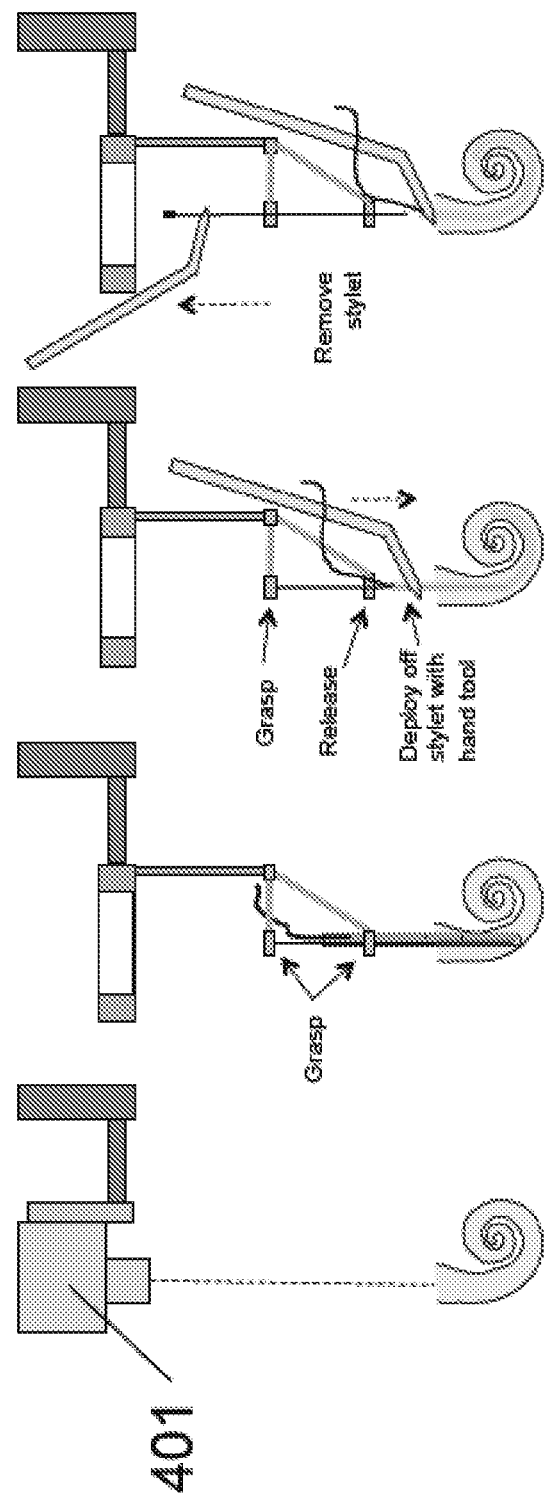
FIG. 4 illustrates an alternative workflow using a bulk OCT scanner or ultrasound scanner to image the cochlea.

FIG. 4 illustrates one alternative workflow in which a bulk OCT or ultrasound imaging scanner 401 is used to form an image of the scala without the necessity of inserting an imaging probe into the scala.

Figure 5:
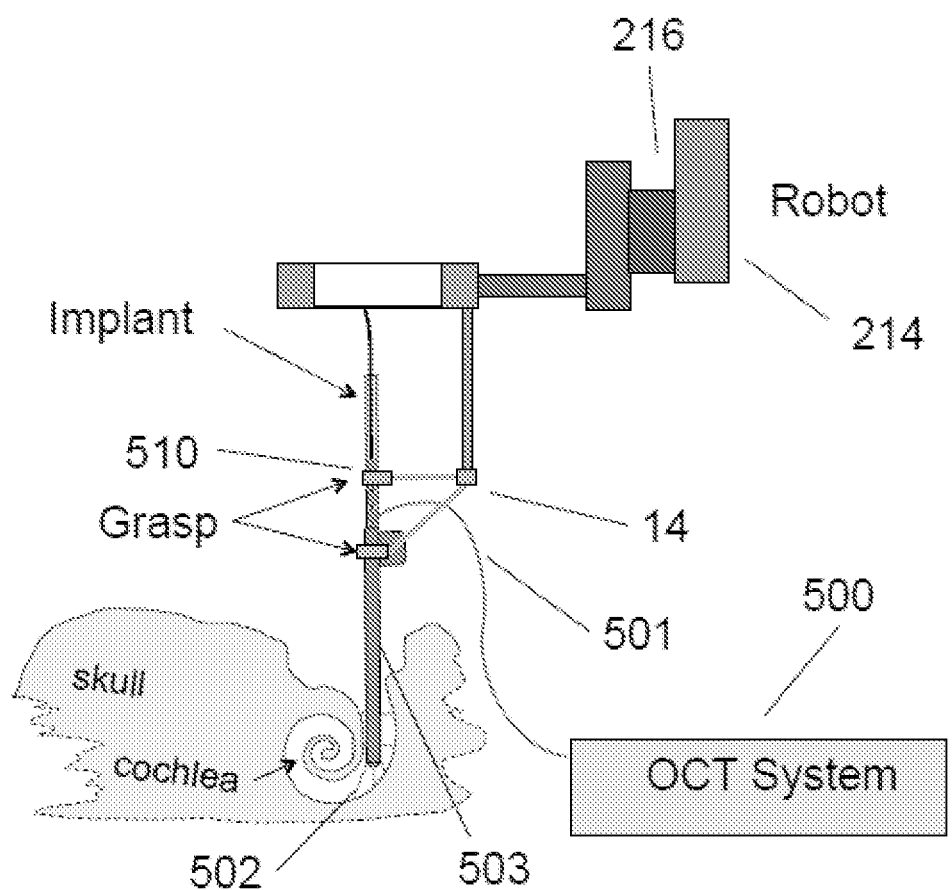
FIG. 5 illustrates an alternative concept in which a sheath is used to provide input for a virtual fixture for robot-assisted insertion into the cochlea.

FIG. 5 illustrates another embodiment in which a sheath is used as the implant delivery device to assist in inserting an implant into the cochlear scalae. Once the sheath and implant are inserted to the desired position and orientation, the implant may be released by the tool holder 14 at the implant grasping point 510 and hand tools (not shown) or a robotic apparatus (also not shown) may be used to deploy the implant. The sheath may then be released and withdrawn from the cochlea either with hand tools or with aid of the robot.

Although the present disclosure describes a particular stylet or sheath based electrode array, and a particular workflow using an OCT probe to image and model the scala, it should be understood that the present invention relates to a variety of tooling and systems and can be readily adapted to a variety of implants and imaging approaches.

Accordingly, a novel sensing system and methods for preventing damage to the scala during cochlear implant surgery are disclosed, using optical sensing to determine the distance of a stylet or the end of the implant itself from the interior wall of the scalar tympani. A variety of feedback methods are proposed to enable the surgeon to perform the procedure safely without damage to the basilar membrane or other delicate anatomic structures. Although a number of embodiments are disclosed, one preferred embodiment comprises a robotically manipulated end-effector.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for robotically assisted implant surgery for cooperatively controlled robots, comprising:
    scanning a narrow cavity in a patient's body with an imaging device;
    forming a model of the narrow cavity;
    removing the imaging device from the narrow cavity;
    using a cooperatively controlled robot to manipulate an implant and an implant delivery device into the narrow cavity; and
    using the model of the narrow cavity to implement virtual fixtures and to manipulate the implant and implant delivery device into the narrow cavity.

2. The method of claim 1 further comprising displaying the models on a display to assist in insertion.

3. The method of claim 1, wherein the robot is used to manipulate an implant and implant delivery device.

4. The method of claim 1, wherein the implant is released by the robot before the implant delivery device is released.

5. The method of claim 4, wherein a hand tool is used to deploy the implant off of the implant delivery device while holding the implant delivery device remains fixed with the robot.

6. The method of claim 5, wherein the stylet or sheath is released, after the implant is deployed off of the implant delivery device.

7. The method of claim 6, further comprising using the hand tool to release the implant delivery device.

8. The method of claim 1, wherein the implant surgery is cochlear implant surgery.

9. The method of claim 8, wherein the cavity is a scala of the cochlea of the patient.

10. The method of claim 9, further comprising modeling the scala of the patient to the first turn.

11. The method of claim 1 wherein the imaging device comprises an imaging probe.

12. The method of claim 1 wherein the imaging device comprises an OCT scanning device.

13. The method of claim 12 wherein the OCT scanning device is further configured to imaging the narrow cavity from a point outside of the narrow cavity.

14. The method of claim 13 wherein the OCT scanning device further comprises a surgical microscope configured such that the OCT scanning device images the narrow cavity and fiducial geometry through the surgical microscope.

15. The method of claim 1 wherein the imaging device comprises an ultrasound imaging device.

16. The method of claim 1 further comprising controlling the cooperatively controlled robot using steady-hand robot control.

17. The method of claim 16 further comprising modifying the steady-hand robot control using virtual fixtures.

18. The method of claim 1 further comprising controlling the cooperatively controlled robot using teleoperation.

19. The method of claim 18 further comprising modifying the teleoperation using virtual fixtures.

20. The method of claim 1 wherein the imaging device comprises at least one of x-ray, cone-beam CT, conventional CT registered to the robot and the patient, or any imaging modality providing 3D images of the narrow cavity registered to the robot and the patient.

21. The method of claim 1 wherein the implant delivery device takes the form of a stylet.

22. The method of claim 1 wherein the implant delivery device takes the form of a sheath.

23. A system for robotically assisted implant surgery for a cooperatively controlled robot, comprising:
a tool holder for receiving a surgical tool, imaging device, or implant adapted to be held by the cooperatively controlled robot and a surgeon;
an imaging device for scanning a narrow cavity in a patient's body; and
a processor for forming a model of the cavity based upon images from the imaging device.

24. The system of claim 23 further comprising a display operatively connected to the processor for displaying the model of the cavity to the surgeon.

25. The system of claim 23 further comprising a first grasping arm for holding an implant delivery device during the robotically assisted implant surgery.

26. The system of claim 25 wherein the implant delivery device further comprises a stylet.

27. The system of claim 25 wherein the implant delivery device further comprises a sheath.

28. The system of claim 23 further comprising a second grasping arm for holding an electrode array of an implant.

29. The system of claim 23 further comprising a surgical microscope configured for viewing a surgical field of the robotically assisted implant surgery.

30. The system of claim 29 wherein the surgical microscope is further configured to show the surgical field on the display.

31. The system of claim 29 wherein the surgical microscope is operatively connected to the processor.

32. The system of claim 23 wherein the processor further comprises a non-transitory computer readable medium programmed to execute at least one of the following functions such as video acquisition from the surgical microscope and other sources, video image processing, stereo and monoscopic video display with graphic overlays, capture of sensor and image data from OCT and other devices, control of robots and other devices, higher-level functions such as virtual fixtures & auditory cues, and the ability to generate a time-stamped, synchronized log of all information and activity during the surgery.

33. The system of claim 23, wherein the imaging device further comprises a probe for insertion into the narrow cavity in the patient's body.

34. The system of claim 23 wherein the imaging device comprises an imaging probe.

35. The system of claim 23 wherein the imaging device comprises an OCT scanning device.

36. The system of claim 35 wherein the OCT scanning device is further configured to imaging the narrow cavity from a point outside of the narrow cavity.

37. The system of claim 35 wherein the OCT scanning device further comprises a surgical microscope configured such that the OCT scanning device images the narrow cavity and fiducial geometry through the surgical microscope.

38. The system of claim 23 wherein the imaging device comprises an ultrasound imaging device.

39. The system of claim 23 wherein the tool holder is calibrated such that a position of a scan resulting from the imaging device is known relative to coordinates of the robot.

40. The system of claim 23 further comprising controlling the cooperatively controlled robot using steady-hand robot control.

41. The system of claim 40 further comprising modifying the steady-hand robot control using virtual fixtures.

42. The system of claim 23 further comprising controlling the cooperatively controlled robot using teleoperation.

43. The system of claim 42 further comprising modifying the teleoperation using virtual fixtures.

44. The system of claim 23 wherein the imaging device comprises at least one of x-ray, cone-beam CT, conventional CT registered to the robot and the patient, or any imaging modality providing 3D images of the narrow cavity registered to the robot and the patient.

45. A tooling device for cooperatively controlled robots, comprising:
a tool holder, a surgical tool, imaging device, or implant adapted to be held by a robot and a surgeon;
a first grasper for holding an implant delivery device;
a second grasper for holding an electrode array of an implant, said second grasper including means for allowing engagement and disengagement of said electrode array; and
wherein said first and second graspers are mounted on a rotational stage, said rotational stage including an aperture along an axis of a microscope to be viewed by the surgeon.

46. The tooling device of claim 45, further including an attachment point for an imaging probe scan motor.

47. The tooling device of claim 45, wherein the first grasper further comprises a means allowing for engagement and disengagement of said stylet.

48. The tooling device of claim 45, wherein the rotational stage further comprises robotic control.

49. The tooling device of claim 45 wherein the rotational stage further defines an opening such that a surgical microscope can be used to visualize a surgical field through the opening.

50. The tooling device of claim 45 further comprising a force sensor for guiding the robot.

51. The tooling device of claim 45 wherein the implant delivery device further comprises a stylet.

52. The tooling device of claim 45 wherein the implant delivery device further comprises a sheath.

* * * * *